(12) United States Patent
Surber et al.

(10) Patent No.: US 8,221,485 B2
(45) Date of Patent: Jul. 17, 2012

(54) CATHETER AND SYSTEM FOR INTRODUCING AN INTRALUMINAL ENDOPROSTHESIS

(75) Inventors: Bettina Surber, Gachnang (CH); Thomas Nef, Ried b. Neerach (CH)

(73) Assignee: Biotronik VI Patent AG, Baar (CH)

( * ) Notice: Subject to any disclaimer, the term of this patent is extended or adjusted under 35 U.S.C. 154(b) by 536 days.

(21) Appl. No.: 12/398,406

(22) Filed: Mar. 5, 2009

(65) Prior Publication Data
US 2009/0228091 A1 Sep. 10, 2009

(30) Foreign Application Priority Data
Mar. 5, 2008 (DE) .......... 10 2008 012 744

(51) Int. Cl.
*A61F 2/06* (2006.01)
*A61F 11/00* (2006.01)
*A61M 29/00* (2006.01)
(52) U.S. Cl. ....................................... 623/1.11
(58) Field of Classification Search ........ 623/1.11–1.13; 606/108, 194
See application file for complete search history.

(56) References Cited

U.S. PATENT DOCUMENTS

| | | | |
|---|---|---|---|
| 5,860,974 A * | 1/1999 | Abele | 606/41 |
| 6,702,802 B1 | 3/2004 | Hancock et al. | |
| 7,022,106 B2 | 4/2006 | Jorgensen | |
| 7,815,975 B2 * | 10/2010 | Pursley | 427/421.1 |
| 2003/0120207 A1 | 6/2003 | Wang | |
| 2005/0154414 A1 | 7/2005 | Perreault et al. | |
| 2007/0016132 A1 | 1/2007 | Oepen et al. | |
| 2007/0250149 A1 | 10/2007 | Von Oepen et al. | |

FOREIGN PATENT DOCUMENTS

| | | |
|---|---|---|
| EP | 0408198 A1 | 1/1991 |
| EP | 0846472 A1 | 6/1998 |
| EP | 1327422 A1 | 7/2003 |
| WO | 03035159 A2 | 5/2003 |

OTHER PUBLICATIONS

Search Report for European Patent Application No. 09150368.0; Jul. 29, 2009.
Search Report for German Patent Application No. 10 2008 012 744.2; Nov. 11, 2008.

* cited by examiner

*Primary Examiner* — Gary Jackson
*Assistant Examiner* — Michael Mendoza
(74) *Attorney, Agent, or Firm* — Greer, Burns & Crain, Ltd.

(57) ABSTRACT

A catheter (10) having an internal tube (13) and an external tube (14) which at least sectionally encloses the internal tube (13). The external tube (14) is connected to a balloon (16) having an endoprosthesis section (18) which positions an intraluminal endoprosthesis (20). The catheter (10) has stiffening means (31, 33, 34, 35) located in the area of at least one end of the endoprosthesis section (18) in its longitudinal direction on the internal tube (13). Also disclosed is a system comprising an intraluminal endoprosthesis (20) and a catheter (10) used for introducing an intraluminal endoprosthesis (20), preferably a stent, into a body cavity.

12 Claims, 2 Drawing Sheets

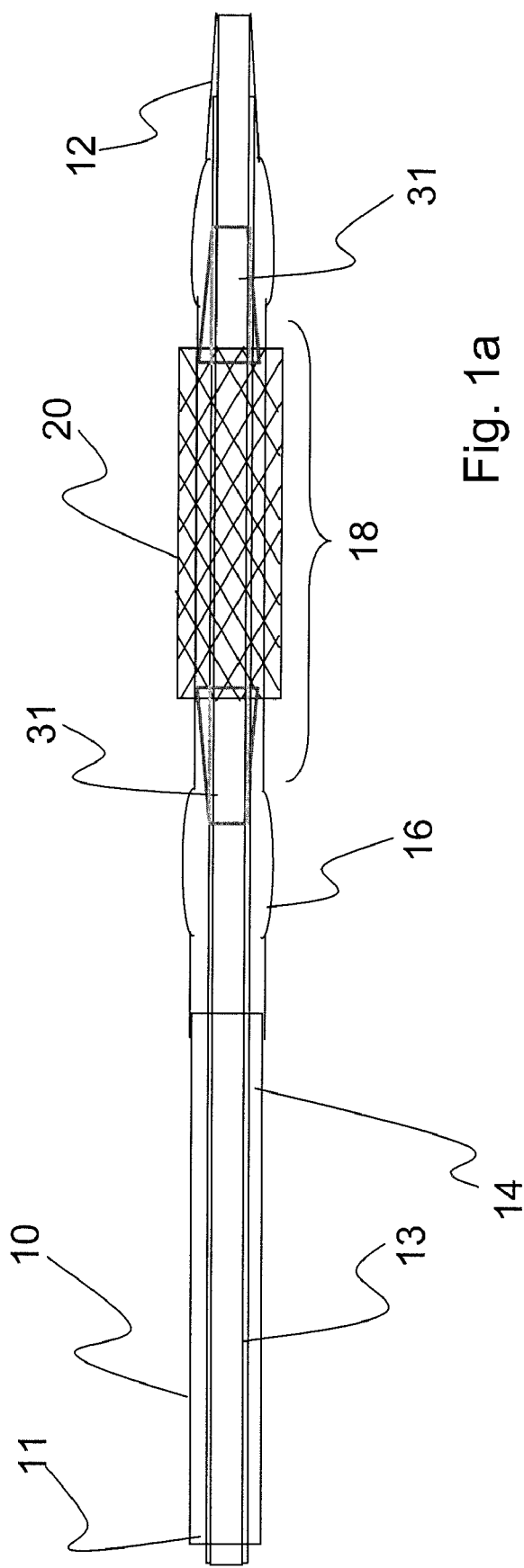
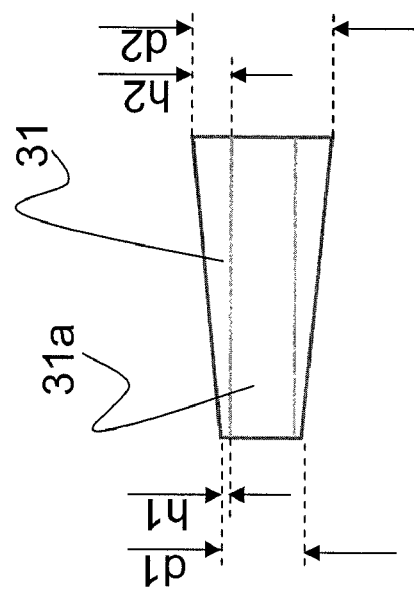
Fig. 1a
Fig. 1b

CATHETER AND SYSTEM FOR INTRODUCING AN INTRALUMINAL ENDOPROSTHESIS

PRIORITY CLAIM

This patent application claims priority to German Patent Application No. 10 2008 012 744.2, filed Mar. 5, 2008, the disclosure of which is incorporated herein by reference in its entirety.

FIELD

The present disclosure relates to a catheter having an internal tube and an external tube which at least partially encloses the internal tube, the external tube being connected to a balloon having an endoprosthesis section which is used to position an intraluminal endoprosthesis. The present disclosure also relates to a system for introducing an intraluminal endoprosthesis, preferably a stent, into a body cavity, the system comprising the intraluminal endoprosthesis and a catheter as disclosed herein.

BACKGROUND

Catheters are small pipes or tubes of various diameters which may be inserted into the particular body cavity to be treated. So-called balloon catheters, which are used above all to expand or reopen a vessel in angioplasty, have a guide wire which is first inserted into the vessel to be treated. A tube which has a non-dilated, folded balloon in a predefined area of the tube is then advanced along the guide wire up to the location of the vessel to be treated so that the balloon is placed in the area of the location of the vessel to be treated, which has a stenosis, for example. The balloon is then dilated, i.e., unfolded and expanded, so that the location to be treated is reopened or expanded and the flow of the bodily fluid in the vessel is no longer obstructed or is no longer obstructed to the previous extent. Finally, the balloon is deflated and removed from the vessel along the guide wire. The guide wire is also retracted from the vessel simultaneously or subsequently.

To achieve optimum properties in regard to flexibility and pushability, catheters currently being used frequently have an internal tube and an external tube which at least partially encloses the internal tube. For purposes of the present disclosure, the term "pushability" means the property of a catheter to transmit longitudinal forces from the proximal end of the catheter to its distal end without forming kinks. Internal and external tubes comprise identical or different materials, such as a polyamide. The balloon of the catheter is connected to the distal end of the external tube, in particular, the balloon is welded thereon.

Balloon catheters are frequently used not only for dilation of a vessel but also for the purpose of introducing intraluminal endoprostheses at a location to be treated in a body cavity. For this purpose, the balloon of a catheter of this type has an endoprosthesis section which is used for positioning an intraluminal endoprosthesis. The endoprosthesis section is the cylindrical section of the balloon, which does not have to be longer than the endoprosthesis. This section is possibly somewhat longer, but only slightly, than the endoprosthesis. The intraluminal endoprosthesis, preferably a stent, is crimped onto the balloon of the catheter in this section and inserted as a system therewith jointly into the body cavity. When the endoprosthesis has reached the intended location after the insertion, the endoprosthesis is expanded together with the balloon of the catheter and remains in the treated vessel after the deflating and folding of the balloon.

Intraluminal endoprostheses, preferably in the form of stents, are currently widely used because intraluminal endoprostheses allow a simple and cost effective treatment for vascular illnesses. Intraluminal endoprostheses frequently have a tubular or hollow-cylindrical main lattice which is open on both longitudinal ends. The main lattice of an endoprosthesis of this type is inserted using a catheter into the body cavity to be treated and is used after removal of the catheter for supporting the body cavity. Constricted areas in the vessels may be expanded permanently or at least over a specific period of time by the use of stents, so that an increase of lumen in the body cavity results.

Intraluminal endoprostheses are frequently also provided with pharmaceutically active substances which are released over a specific period of time in the organism.

These pharmaceutically active substances may be used, for example, for preventing restenosis or agglomerations. It is possible through the release of pharmaceutically active substances with which intraluminal endoprostheses of this type are provided to perform only a local treatment, i.e., an elution of an active ingredient essentially only in the tissue surrounding the intraluminal endoprosthesis. This procedure is also referred to as "local drug delivery" (LDD). The treatment location at which the active ingredient is to unfold its pharmacological effect directly adjoins the location of the implantation of the intraluminal endoprosthesis.

For purposes of the present disclosure, a "pharmaceutically active substance" (or therapeutically active or active substance) means a vegetable, animal, or synthetic active ingredient (medication) or a hormone which is used in suitable dosing as a therapeutic agent for influencing states or functions of the body as a replacement for natural active ingredients produced by the human or animal body, such as insulin, and for removing or making harmless pathogens, tumors, cancer cells, or materials foreign to the body. The release of the substance in the surroundings of the endoprosthesis has a positive effect on the course of healing or counteracts pathological changes of the tissue as a result of the surgical intervention and/or is used to make diseased cells harmless in oncology.

For example, pharmaceutically active substances of this type have an anti-inflammatory and/or antiproliferative and/or spasmolytic effect by which restenosis, inflammations, or (vascular) spasms may be avoided, for example. Substances of this type may comprise, in especially preferred exemplary embodiments, one or more substances of the active ingredient groups of calcium channel blockers, lipid regulators (such as fibrates), immunosuppressive agents, calcineurin inhibitors (such as tacrolimus), antiphlogistics (such as cortisone or diclofenac), anti-inflammatory agents (such as imidazoles), antiallergy agents, oligonucleotides (such as dODN), estrogens (such as genistein), endothelium producers (such as fibrin), steroids, proteins, hormones, insulins, cytostatics, peptides, vasodilators (such as sartanes), and agents having an antiproliferative effect, such as paclitaxel or sirolimus.

Currently, intraluminal endoprostheses which comprise a material subject to biodegradation are also used. For purposes of the present disclosure, biodegradation mean hydrolytic, enzymatic, or other metabolically-related degradation processes in the living organism which are caused by the bodily fluids coming into contact with the endoprosthesis and result in gradual dissolving of at least large parts of the endoprosthesis. For purposes of the present disclosure, the term biocorrosion is frequently used synonymously with the term biodegradation. For purposes of the present disclosure, the term bioresorption comprises the subsequent resorption of the degradation products by the living organism. Biodegradable materials of this type may be implemented from polymers or metals. In connection with stents, the abbreviation "AMS" (absorbable metal stent) is also common. Stents of this type contain a biodegradable metal, preferably magnesium and/or a magnesium alloy.

In addition, providing intraluminal endoprostheses with functional elements, which have a different material composition in comparison to the material of the main lattice in at least a part of their volume, is known. These functional elements are used to determine the position of an endoprosthesis in the body or to release medications, for example.

The ascertainment of the position of an endoprosthesis is frequently performed using imaging methods, for example, using an x-ray radiation device. Because the materials employed for the main lattice of endoprostheses of this type typically only absorb x-ray radiation to a small extent, i.e., are x-ray translucent or radiolucent, the endoprostheses are frequently provided with so-called x-ray markers which contain a material which has a higher absorption of the x-ray radiation (x-ray opaque or radioopaque material).

In a catheter which is used to introduce an intraluminal endoprosthesis, such as a stent, the problem frequently exists that rigidity jumps arise on the ends of a stent attached to such a catheter. In particular, if the stent is rigid or has a high rigidity due to a large crimping diameter, the danger exists that the catheter will be kinked at the rigidity jumps in curves of the body cavity which the catheter passes and thus jam the guide wire. The friction between catheter and guide wire may thus increase. If the stent additionally has x-ray markers on the stent ends, the danger exists that the x-ray markers will protrude in curves due to the kinking of the catheter and thus will remain hanging in the body cavity or on the guide catheter.

A balloon catheter is disclosed in U.S. Pat. No. 7,022,106, in which an increase of the feed force which is transmitted by the external tube to the distal end of the catheter is achieved. For this purpose, the known catheter has an external tube and an internal tube which extends coaxially in the external tube. In addition, a balloon is situated in proximity to the distal end of the catheter. The balloon is fastened at its proximal fastening point to the external tube and is connected to the internal tube at its distal fastening point. Moreover, the external tube may be reinforced to increase its rigidity and pushability along this segment of the catheter. In one exemplary embodiment of the known catheter, the external tube tapers step-by-step starting from the proximal fastening point in the distal direction and forms a conical section. The disadvantage of this known catheter is that the construction has a design which is quite complicated, making the catheter costly to produce. In addition, the known catheter does not solve the problem described above because the rigidity jumps at the stent ends are not remedied by the known design.

A further known catheter is described in U.S. Patent Publication No. 2007/0016132. This catheter has an oblong body having a proximal section and a distal section. Furthermore, a plurality of stiffening means are provided on the catheter which are used to vary the rigidity along the catheter body. Various types of stiffening means are explained in the publication which overlap or have a varying rigidity along the length of the catheter body, for example. For this purpose, the stiffening means situated along the length of the body of the catheter may comprise various materials which have a varying flexibility. However, the publication does not concern itself with the problem of the rigidity jumps at the endoprosthesis ends when an intraluminal endoprosthesis is introduced into a body cavity using the catheter.

SUMMARY

The present disclosure describes several exemplary embodiments of the present invention.

One aspect of the present disclosure provides a catheter, comprising a) an internal tube; b) an external tube which at least sectionally encloses the internal tube; c) a balloon having an endoprosthesis section which can position an intraluminal endoprosthesis, the balloon being connected to the external tube; and d) stiffening means proximate to at least one end of the endoprosthesis section in its longitudinal direction on the internal tube.

Another aspect of the present disclosure provides a system for introducing an intraluminal endoprosthesis, preferably a stent, into a body cavity, comprising a) an intraluminal endoprosthesis, and b) a catheter comprising i) an internal tube; ii) an external tube which at least sectionally encloses the internal tube; iii) a balloon having an endoprosthesis section which can position an intraluminal endoprosthesis, the balloon being connected to the external tube; and iv) stiffening means proximate to at least one end of the endoprosthesis section in its longitudinal direction on the internal tube, wherein the intraluminal endoprosthesis is located in the endoprosthesis section on the balloon, the endoprosthesis being crimped externally onto the endoprosthesis section of the balloon.

One aspect of the present disclosure provides a catheter for introducing an intraluminal endoprosthesis in which rigidity jumps are avoided. Furthermore, the present disclosure provides a corresponding system for introducing an intraluminal endoprosthesis.

The above feature is achieved by a catheter in which stiffening means are situated in the area of at least one end of the endoprosthesis section in its longitudinal direction on the internal tube. The direction in which the longitudinal axis of the catheter extends is referred to as the longitudinal direction in this case. The specified area of the end of the endoprosthesis section comprises both a short section having a length of approximately 2 mm to approximately 15 mm of the catheter, which adjoins the endoprosthesis section in the longitudinal direction, but is outside the endoprosthesis section and also the particular adjoining end section of the endoprosthesis section. By stiffening means of this type, which are situated in the area of one end or both ends of the endoprosthesis section in its longitudinal direction, the internal tube of the catheter is locally stiffened and an essentially continuous rigidity transition of the entire area comprising internal tube, balloon, and stent is provided so that a rigidity jump no longer exists in this area.

In an especially preferred exemplary embodiment, the stiffening means are implemented as a polymer tube which is preferably welded to the internal tube or glued onto the internal tube. Stiffening means of this type may be produced particularly cost-effectively and situated easily and in a precise position on the internal tube.

The polymer tube preferably contains one or more polymers from the group consisting of polyamides and PEBAX® (polyether block amide). These polymers have especially good properties in regard to the interaction with the remaining components of the catheter.

In an especially preferred exemplary embodiment, the polymer tube has an external diameter which enlarges essentially continuously from its end in the longitudinal direction, which is situated outside the endoprosthesis section, up to its end in the longitudinal direction, which is situated inside or precisely at the edge of the endoprosthesis section. The enlargement of the external diameter is connected to an enlargement of the wall thickness of the polymer tube corresponding to the enlargement of the external diameter so that the rigidity of the polymer tube also increases in this direction. An especially simple and cost-effective rigidity transition may be implemented in the areas of the ends of the endoprosthesis section in this way.

It is also preferable if the material of the polymer tube contains at least one x-ray opaque (radiodense) material, such as a filler made of barium, bismuth, or tungsten. This exemplary embodiment allows a separate x-ray marker, which comprises platinum, for example, to be dispensed with.

In a further exemplary embodiment, the stiffening means have a metal ring or multiple metal rings which are provided at a predetermined length and/or spacing adapted to the rigidity jump generated by the particular intraluminal endoprosthesis, the one metal ring or the metal rings preferably being crimped onto the internal tube. A rigidity transition may also be achieved by simple, cost-effective means through such a configuration, in particular, of multiple metal rings, in the area of the end of the endoprosthesis section, materials preferably being used which are visible upon x-ray irradiation, so that these rings may be used as marking rings for the x-ray visibility.

The metal ring or the metal rings especially preferably contain one or more metals from the group consisting of platinum and iridium. These metals have especially good rigidity properties and may be used as the marking under x-ray irradiation.

Especially preferably, 1 to 5 metal rings are provided which have a length of approximately 0.1 mm to 1 mm and/or a spacing of approximately 0.1 mm to 1 mm.

The above feature is also achieved by a system for introducing an intraluminal endoprosthesis which comprises the intraluminal endoprosthesis and a catheter, the catheter having the properties described hereinabove and the intraluminal endoprosthesis being situated in the endoprosthesis section on the balloon, the endoprosthesis preferably being externally crimped on the endoprosthesis section of the balloon. Using a system of this type, rigidity jumps at the ends of the endoprosthesis are avoided and a rigidity transition is provided which avoids kinking of the catheter upon introduction of the endoprosthesis into the body cavity. X-ray markers situated on the ends of the endoprosthesis may thus also be prevented from remaining hanging in the body cavity by a system herein disclosed.

In a preferred exemplary embodiment, the endoprosthesis has an x-ray marker on at least one of its ends situated in the longitudinal direction. The location of the endoprosthesis may be detected and checked upon an irradiation using x-ray radiation by an x-ray marker of this type.

In a further preferred exemplary embodiment, the endoprosthesis has a pharmaceutically active substance, the pharmaceutically active substance advantageously being able to be introduced directly at the location of the use of the endoprosthesis and side effects thus being avoided. Alternatively or additionally, the endoprosthesis may at least partially comprise a degradable material.

BRIEF DESCRIPTION OF THE DRAWINGS

Further goals, features, advantages, and possible applications of the invention disclosed herein result from the following description of exemplary embodiments on the basis of the figures. All features which are described and/or shown in the drawings form the subject matter of the present disclosure alone or in arbitrary combinations, even independently of their summary in the individual claims.

Various aspects of the present disclosure are described hereinbelow with reference to the accompanying figures.

FIG. 1a shows a first exemplary embodiment of a system one exemplary embodiment of the present disclosure comprising a catheter, which is shown in longitudinal section, and a stent, which is shown in a view from the side;

FIG. 1b shows a longitudinal section of stiffening means of the system shown in FIG. 1a.

DETAILED DESCRIPTION

Figure 2:
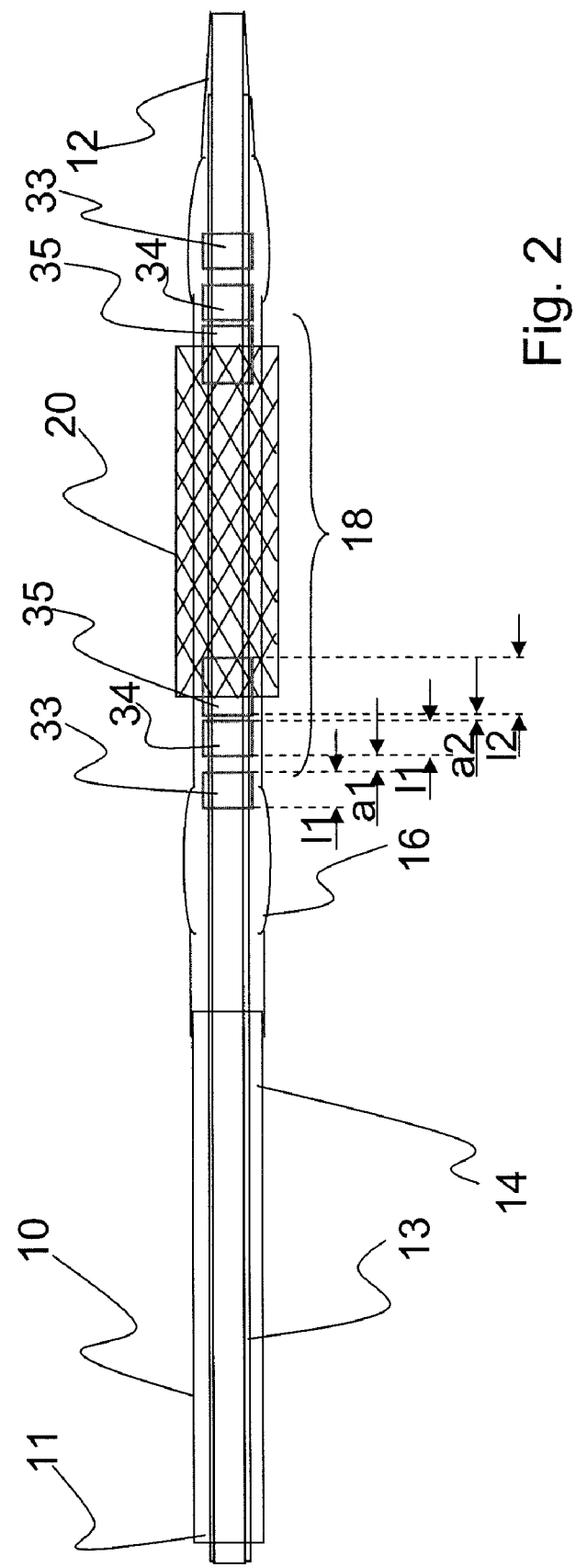
FIG. 2 shows a second exemplary embodiment of a system according to the present disclosure made of a catheter and a stent, the catheter being shown in a longitudinal section and the stent being shown in a view from the side.

FIG. 1a shows a distal end section of a catheter 10 having a proximal end 11 and a distal end 12 of the end section in longitudinal section. The catheter 10 has a guide wire (not shown) as well as an internal tube 13 and an external tube 14. The internal tube 13 is situated coaxially inside the external tube 14 so that the external tube 14 encloses the internal tube 13.

A balloon 16 is welded on the distal end of the external tube 14 or is connected thereto and/or is fastened thereon in another way. The balloon can be expanded in diameter by filling with a contrast agent/saline mixture. The balloon 16 also encloses the internal tube 13. The endoprosthesis section 18, in which the stent 20 is situated, is provided on the balloon 16. The stent 20 is crimped onto the balloon 16 in the area of the endoprosthesis section 18 of the catheter 10.

The internal tube 13 has a polymer tube 31 welded to the internal tube 13 as stiffening means in each case on the distal and proximal ends of the endoprosthesis section 18 situated in the longitudinal direction, which is shown in greater detail in the longitudinal section in FIG. 1b.

The polymer tube 31 is implemented essentially in the form of a truncated cone in its external shape and has a first external diameter d1 at one end and a second external diameter d2 at a second end. The first external diameter d1 is smaller than the second external diameter d2 in this case. In addition, the polymer tube has a through opening 31a which is implemented as cylindrical and allows the polymer tube 31 to be situated on the internal tube 13.

In the polymer tube 31 situated at the proximal end of the endoprosthesis section 18, the first diameter d1 is situated at the proximal end of the polymer tube 31. In the polymer tube 31 provided at the distal end of the endoprosthesis section 18, the first external diameter d1 is located at the distal end of the polymer tube 31, the ends of the polymer tube 31 having the first external diameters d1 being situated slightly outside the endoprosthesis section 18 in each case. The ends of the polymer tube 31 having the second external diameter d2 are situated opposite thereto inside the endoprosthesis section 18. In a further exemplary embodiment, the ends of the polymer tube 31 having the second external diameters d2 may also be situated directly at the edge of the endoprosthesis section 18. The polymer tube 31 has a first wall thickness h1 in the area of the first external diameter d1 and a second wall thickness h2 in the area of the second external diameter d2. The wall thickness h1 is less than the second wall thickness h2, so that the polymer tube 31 has a lower rigidity in the area of the first external diameter d1 than in the area of the second external diameter d2. The rigidity increases continuously along the longitudinal direction of the polymer tube 31, i.e., along the direction of its longitudinal axis, from the end of the polymer tube 31 having the first external diameter d1 up to the area having the second external diameter d2.

In a second exemplary embodiment of the system according to the present disclosure made of catheter 10 and stent 20, shown in FIG. 2, three metal rings 33, 34, and 35 are provided instead of the polymer tubes 31 as the stiffening means in the longitudinal direction at each of both ends of the endoprosthesis section 18. The metal rings 33, 34, and 35 preferably contain at least one metal from the group consisting of platinum and iridium and are preferably crimped onto the internal tube 13.

The metal rings 33, 34, and 35 are situated on the proximal end of the endoprosthesis section 18 in this sequence in the direction of the distal end. The metal rings 33, 34, and 35 are situated in the reverse sequence on the distal end of the endoprosthesis section 18, the metal rings 33 and 34 each being situated partially outside the endoprosthesis section 18 at both ends. The metal ring 35 is provided inside the endoprosthesis section 18 in each case. The metal rings 33 and 34 each have a length 11 in the longitudinal direction of 0.5 mm, while the metal ring 35 has a length 12 of 1 mm. The metal rings 33 and 34 have a spacing a1 of 0.5 mm and the metal rings 34 and 35 have a spacing a2 of 0.3 mm. By a selection of the length of the metal rings 33, 34, and 35 and/or of the spacing of these metal rings of this type, an especially advantageous rigidity transition may be achieved at the ends of the endoprosthesis section 18.

All patents, patent applications and publications referred to herein are incorporated by reference in their entirety.

What is claimed is:

1. A catheter, comprising:
   a) an internal tube;
   b) an external tube which at least sectionally encloses the internal tube;
   c) a balloon having an endoprosthesis section having a proximal end and a distal end which can position an intraluminal endoprosthesis, the balloon being connected to the external tube; and
   d) a first set of metal rings positioned proximate to the endoprosthesis proximal end and a second set of metal rings positioned proximate to the endoprosthesis distal end, the first and second sets of rings crimped onto the internal tube, at least two rings in each set having different lengths from each other, the first and second sets of rings being provided at predetermined spacings so as to provide a rigidity transition at the proximal and distal ends, respectively, of the endoprosthesis section.

2. The catheter of claim 1, wherein the first and second sets of metal rings are made of one or more metals from the group consisting of platinum and iridium.

3. The catheter of claim 1, wherein the number of metal rings in each set of rings is from 2 to 5, the rings having either a length of approximately from 0.1 mm to 1 mm or a spacing of approximately from 0.1 mm to 1 mm, or both.

4. The catheter of claim 1 wherein the metal rings are made of a material visible upon x-ray irradiation.

5. The catheter of claim 1 wherein there are at least three rings in the first set or the second set or both, and wherein a distance between the first ring and the second ring is different from a distance between the second ring and the third ring.

6. A system for introducing an intraluminal endoprosthesis, preferably a stent, into a body cavity, comprising:
   a) an intraluminal endoprosthesis, and
   b) a catheter comprising:
      i) an internal tube;
      ii) an external tube which at least sectionally encloses the internal tube;
      iii) a balloon having an endoprosthesis section which can position an intraluminal endoprosthesis, the balloon being connected to the external tube; and
      iv) a first set of metal rings positioned proximate to the endoprosthesis proximal end and a second set of metal rings positioned proximate to the endoprosthesis distal end, the first and second sets of rings crimped onto the internal tube, at least two rings in each set having different lengths from each other, the first and second sets of rings being provided at predetermined spacings so as to provide a rigidity transition at the proximal and distal ends, respectively, of the endoprosthesis section,
   wherein the intraluminal endoprosthesis is located in the endoprosthesis section on the balloon, the endoprosthesis being crimped externally onto the endoprosthesis section of the balloon.

7. The system of claim 6, wherein the endoprosthesis further comprises an x-ray marker disposed on at least one of the ends of the endoprosthesis in the longitudinal direction.

8. The system of claim 6, wherein the endoprosthesis further comprises a pharmaceutically active substance.

9. The system of claim 6, wherein the first and second sets of metal rings are made of one or more metals from the group consisting of platinum and iridium.

10. The system of claim 6, wherein the number of metal rings in each set of rings is from 2 to 5, the rings having either a length of approximately from 0.1 mm to 1 mm or a spacing of approximately from 0.1 mm to 1 mm, or both.

11. The system of claim 6, wherein the endoprosthesis comprises a degradable material.

12. The system of claim 6 wherein the metal rings are made of a material visible upon x-ray irradiation.

* * * * *